United States Patent [19]

Rault et al.

[11] Patent Number: 5,130,301

[45] Date of Patent: Jul. 14, 1992

[54] PYRROLO (1,2-A) THIENO (2,3-F) (1,4)-DIAZEPINES

[75] Inventors: Sylvain Rault, Moult; Michel Boulouard, Caen; Max Robba, Paris; Béatrice Guardiola; Michelle Devissaguet, both of Neuilly sur Seine, all of France

[73] Assignee: Adir et Compagnie, Courbevoie, France

[21] Appl. No.: 675,420

[22] Filed: Mar. 26, 1991

[30] Foreign Application Priority Data

Mar. 27, 1990 [FR] France ................................ 90 03839

[51] Int. Cl.$^5$ ...................... A61K 31/55; C07D 475/14
[52] U.S. Cl. ..................................... 514/220; 540/496; 540/560
[58] Field of Search .................. 540/496, 560; 514/220

[56] References Cited

PUBLICATIONS

Novel Convenient Synthesis of 1,4–Diazepines, 6-alkoxy-5,6-Dihydro-4H-Pyrrolo [1,2-a] Thieno [3,2-f]-4-Diazepine-4-Ones, S. Rault et al., Heterocycles (1979) 12 (8) pp. 1009–1011.

Pyrrolo [1,2-a] Thieno [3,2-f]-1,4-Diazepines, Novel Synthesis and X-Ray Analysis, S. Rault et al., Tetrahedron Letters (1979)N° 7 pp. 643–644.

Synthesis of 4H-Pyrrolo [1,2-a] Thieno [3,2-f] [1,4] Diazepines, H. Fujimori et al., Journal of Heterocyclic Chemistry (1977) 14 (2) pp. 235–240.

*Primary Examiner*—Robert T. Bond
*Attorney, Agent, or Firm*—Gordon W. Hueschen

[57] ABSTRACT

Novel 4H-pyrrolo[1,2-a]thieno[2,3-f][1,4]diazepine which are usable as a medicinal product and correspond to the general formula (I):

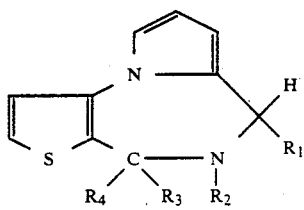

(I)

in which:

$R_1$, $R_2$, $R_3$ and $R_4$ have the same meaning as given in the specification.

These compounds, as well as their physiologically tolerable salts, may be used in therapy, in particular in the treatment of disorders linked to hypoxemia and to certain metabolic disorders.

21 Claims, No Drawings

PYRROLO (1,2-A) THIENO (2,3-F) (1,4)-DIAZEPINES

The present invention relates to novel 4H-pyrrolo [1,2-a]thieno [2,3-f][1,4]diazepine compounds, to their process of preparation and to the pharmaceutical compositions containing them.

It relates especially to the 4H-pyrrolo[1,2-a]-thieno[2,3-f][1,4]diazepine compounds of general formula (I):

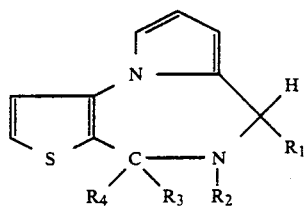

in which:
$R_1$ represents:
a hydrogen atom,
a hydroxyl radical,
a radical of general formula:

$-OR_5$ or $-Sr_5$ in which $R_5$ represents:
an alkyl radical containing 1 to 5 carbon atoms in a straight or branched chain, optionally substituted with a phenyl radical or with a group of formula —COOB in which B represents a hydrogen atom or an alkyl radical containing 1 to 5 carbon atoms, or
an aryl radical such as, for example, a phenyl radical,
a radical of general formula:

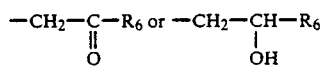

in which $R_6$ represents:
a linear or branched alkyl radical having 1 to 5 carbon atoms,
an aryl radical (optionally substituted with one or more halogen atoms, alkoxy groups having 1 to 3 carbon atoms or trifluoromethyl groups),
an aralkyl radical having 7 to 9 carbon atoms (optionally substituted on the aromatic ring with one or more halogen atoms, alkoxy groups having 1 to 3 carbon atoms or trifluoromethyl groups),
a radical of formula:

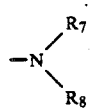

in which:
$R_7$ and $R_8$, which may be identical or different, each represent a hydrogen atom, an alkyl radical containing 1 to 5 carbon atoms in a straight or branched chain, a cycloalkyl radical containing 3 to 5 carbon atoms, an aryl radical (optionally substituted with one or more halogen atoms, alkoxy groups having 1 to 3 carbon atoms or trifluoromethyl groups) or an aralkyl radical having 7 to 9 carbon atoms (optionally substituted on the aromatic ring with one or more halogen atoms, alkoxy groups having 1 to 3 carbon atoms or trifluoromethyl groups), or $R_7$ and $R_8$, together with the nitrogen atom to which they are linked, form a five- or six-membered heterocyclic radical optionally containing another hetero atom such as, for example, a second nitrogen atom or an oxygen atom, and optionally substituted with a linear or branched alkyl radical having 1 to 5 carbon atoms, with an alkoxycarbonyl radical having 2 to 6 carbon atoms or with an aryl radical, an aralkyl radical having 7 to 9 carbon atoms, a heteroaryl radical or a diaralkyl radical such as, for example, a benzhydryl radical (these radicals optionally being substituted on the aromatic ring or rings with one or more identical or different substituents selected from halogen, hydroxyl, alkyl or alkoxy having 1 to 4 carbon atoms, nitro or trifluoromethyl), an alkyl radical containing 1 to 5 carbon atoms, optionally substituted with one or more radicals selected from the group composed of hydroxyl, oxo and cyano radicals and alkoxycarbonyl radicals containing 2 to 4 carbon atoms;

$R_2$ represents:
a hydrogen atom,
an alkyl radical having 1 to 5 carbon atoms in a straight or branched chain,
an arylsulfonyl radical in which the aryl group is optionally substituted with an alkyl radical having 1 to 5 carbon atoms in a straight or branched chain,
an alkyl carbonyl radical having 2 to 3 carbon atoms,
a radical of general formula:

in which
$R_9$ represents a linear or branched alkyl radical having 1 to 6 carbon atoms or an aryl radical or aralkyl radical having 7 to 9 carbon atoms (optionally substituted on the aromatic ring with one or more halogen atoms, alkoxy radicals having 1 to 3 carbon atoms or trifluoromethyl radicals);

$R_3$ and $R_4$ represent:
each simultaneously a hydrogen atom or
together an oxygen atom.

Depending on the meaning of $R_1$, the compounds of general formula (I) possess one or more asymmetric carbon atoms and, as a result, give rise to isomers or diastereoisomers which are also included in the present invention.

The prior art in this field is illustrated, in particular, by: Heterocycles vol 12 No. 8, pages 1009–1011, (1979), Tetrahedron letters No. 7, pages 643–644, (1979), and J. Heter. Chem., 14 No. 2, pages 235–240, (1977), which mention pyrrolo[1,2-a]thieno-[3,2-f][1,4]diazepine compounds not including or in any way suggesting the compounds of the present invention.

The latter, which are pyrrolo[1,2-a]thieno-[2,3-f][1,4]diazepine compounds of novel structure, possess advantageous pharmacological properties. They interfere, in particular, with central benzodiazepine receptors of the peripheral type and exert a pronounced antihypoxic effect, thereby enabling them to be used in the treatment of ischemic syndromes of any localization, acute, transient or progressive, and in the correction of disorders linked to hypoxemia, for example during cerebral ageing.

They also possess substantial hypocholesterolemic, hypotriglyceridemic, hypolipidemic and hypoglycemic properties which make them valuable in the treatment of a large number of pathological disorders.

The subject of the present invention is also the process for preparing the compounds of general formula (I), wherein:

A—either 2-aminocarbonyl-3-(2-formyl-1-pyrrolyl)thiophene of formula (II):

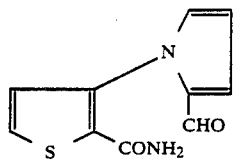

(II)

is treated 1) either with a mixture of water and triethylamine, to give the compound of formula (Ia):

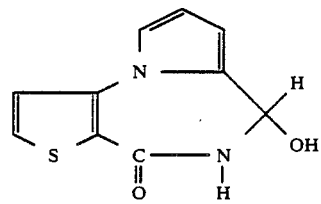

(Ia)

2) or with an alcohol or a thiol of respective general formulae (III) and (IV):

$R_5OH$ (III), $R_5SH$ (IV)

in which $R_5$ has the same meaning as in the compounds of general formula (I), to give the compounds of general formulae (Ib) and (Ic), respectively:

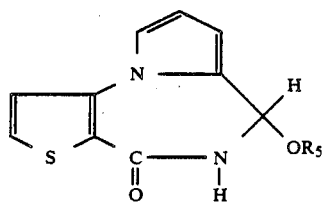

(Ib)

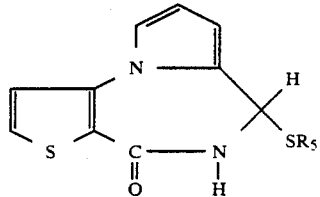

(Ic)

in which $R_5$ has the meaning defined above;

3) or with a secondary amine of general formula (V):

(V)

in which $R_7$ and $R_8$ have the same meanings as in the compounds of general formula (I), to give the compounds of general formula (Id):

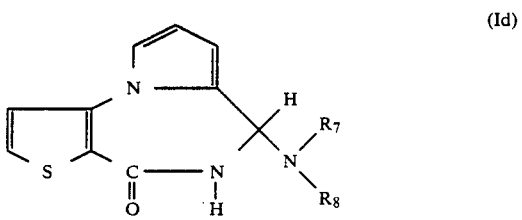

(Id)

in which $R_7$ and $R_8$ have the same meanings as in the compounds of general formula (I);

4) or in an alkaline medium with a methyl ketone of general formula (VI):

(VI)

in which $R_6$ has the same meaning as in the compounds of general formula (I), so as to obtain the compounds of general formula (If):

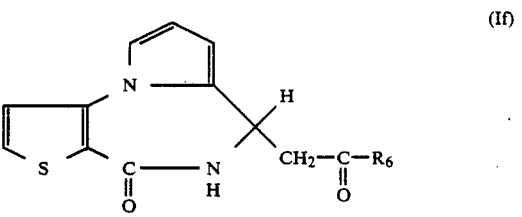

(If)

in which $R_6$ has the same meaning as in the compounds of general formula (I), which can optionally be treated with a sodium borohydride to obtain the compounds of general formula (Ig):

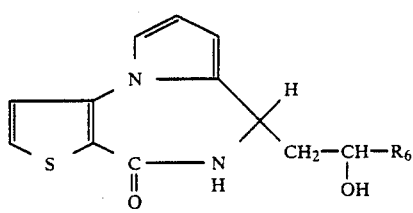  (Ig)

in which $R_6$ has the same meaning as in the compounds of general formula (I);

B—or the compound of general formula (Ia) obtained above is treated:
1) either with an alcohol of general formula (III) defined above, to give the compounds of general formula (Ib):

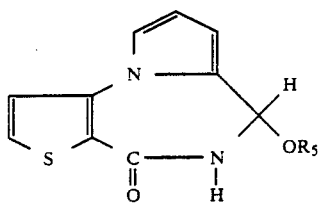  (Ib)

in which $R_5$ has the same definition as in the compounds of general formula (I);

2) or with an amine of general formula (V) defined above, to give the compounds of general formula (Id):

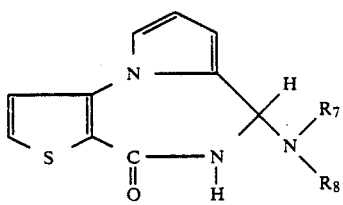  (Id)

in which $R_7$ and $R_8$ have the same meanings as in the compounds of general formula (I), which can optionally be treated with sodium borohydride to obtain the compound of formula (Ie):

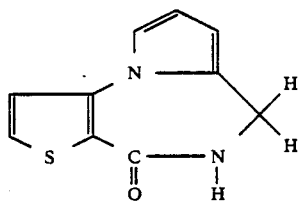  (Ie)

which can optionally be reacted:
a) either with an anhydride of general formula (XI):

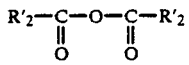  (XI)

in which $R'_2$ represents a methyl or ethyl radical, so as to obtain the compounds of general formula (II):

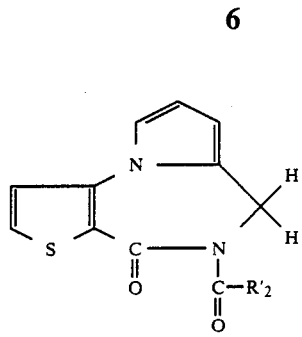  (II)

in which $R'_2$ has the meaning defined above;

b) or with an isocyanate of general formula (XII):

$R_9—N=C=O$  (XII)

in which $R_9$ has the same meaning as in the compounds of general formula (I), so as to obtain the compounds of general formula (Im):

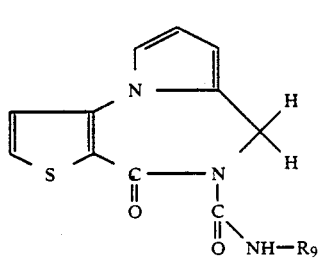  (Im)

in which $R_9$ has the same meaning as in the compounds of general formula (I);

3) or, in an alkaline medium with a methyl ketone of general formula (VI) defined above, to give the compounds of general formula (If):

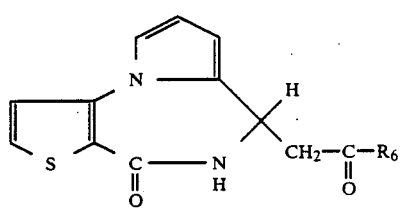  (If)

in which $R_6$ has the same meaning as in the compounds of general formula (I);

4) or, in the presence of triethylamine, with a compound of general formula (VII):

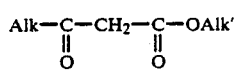

Alk—C—CH$_2$—C—OAlk'  (VII)
    ‖        ‖
    O        O in which Alk and Alk', which may be identical or different, each represent an alkyl radical having 1 to 3 carbon atoms, to give the compounds of general formula (Ih):

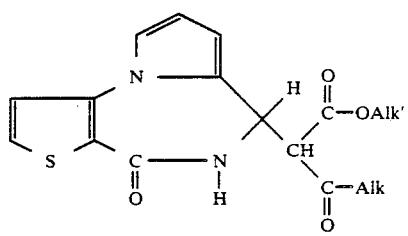
(Ih)

in which Alk and Alk' have the meanings defined above;

5) or, in the presence of triethylamine, with a compound of general formula (VIII):

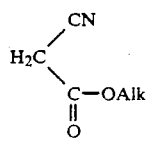
(VIII)

in which Alk has the meaning defined above, to give the compounds of general formula (Ii):

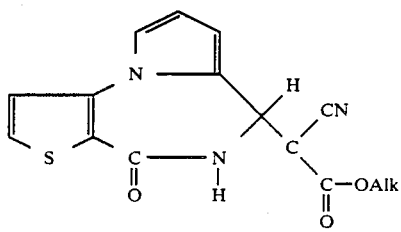
(Ii)

in which Alk has the meaning defined above;

6) or with LiAlH, to give the compound of formula (Ij):

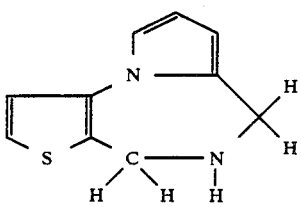
(Ij)

which, when treated a) either with a stoichiometric amount of an inorganic or organic acid, gives the corresponding acid-addition salt;

b) or with an alkyl iodide of general formula (IX):

R''₂ I     (IX)

in which R''₂ represents an alkyl radical having 1 to 5 carbon atoms in a straight or branched chain, gives, depending on the stoichiometric ratio (IX-)/(Ij):

either the compound of general formula (Ik₁):

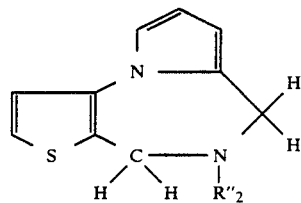
(Ik₁)

in which R''₂ has the meaning defined above, or the dialkylammonium iodide of general formula (In)

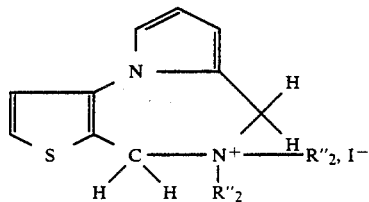
(In)

in which R''₂ has the meaning defined above;

c) or with a halogenated compound of general formula (X):

Hal—R'''₂     (X)

in which R'''₂ represents an arylsulfonyl radical in which the aryl group is optionally substituted with an alkyl radical having 1 to 5 carbon atoms in a straight or branched chain, gives the compounds of general formula (Ik₂):

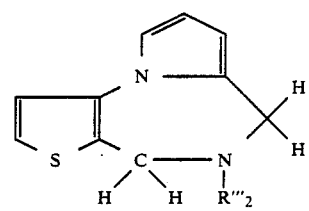
(Ik₂)

in which R'''₂ has the meaning defined above.

All the compounds of formula (Ia) to (Im) are comprised within the compounds of general formula (I).

The compounds of general formula (I) give rise to salts with physiologically tolerable acids. These salts are also included in the present invention.

The compounds of the present invention, as well as their salts, possess advantageous pharmacological and therapeutic properties, in particular potent antihypoxic activity as well as substantial metabolic properties.

During ageing or following a stroke, increased frailty and cell vulnerability are physiopathological components of importance in the search for new therapies directed towards protecting the brain placed in a position of inability to respond to any further stress emanating from its environment.

Such a stress may be reproduced in the form of a defective oxygen supply, and for this reason, in terms of their consequences, there is a close analogy between hypoxia and cerebral ageing.

The compounds of the present invention were tested for their capacity to prolong survival of the cerebral tissue during acute hypoxia in mice. These tests demonstrated that the compounds of the invention have a very potent antihypoxic protective effect, and thus confirmed the great value of their use in therapy.

By clearly counteracting brain death during insufficiency of the oxygen supply, the compounds of the present invention exert a pronounced antihypoxic effect and are hence useful in the case of ischemic syndromes of any localization, acute, transient or progressive, since they exert their pharmacological properties with respect to the oxygen deficiency which accompanies these mishaps. Their pharmacological properties enable them to be applied in the correction of disorders linked to hypoxemia, for example during cerebral ageing.

The compounds of the invention also possess exceptional metabolic properties, being strongly hypolipidemic, hypocholesterolemic, hypotriglyceridemic and hypoglycemic.

When given for 15 days to rats subjected to a hypercholesterolemic diet, they proved to be much more active (at least 30-fold) than clofibrate with respect to the lowering of the plasma triglyceride, cholesterol and HDL (high density lipoprotein)-cholesterol levels.

Moreover, the compounds of the present invention exhibit good hypotensive properties in animals at a dose of 30 mg/kg I.P.

The compounds of general formula (I), as well as their addition salts with a pharmaceutically acceptable inorganic or organic acid such as, for example, hydrochloric, methanesulfonic, citric and maleic acids, may be made into pharmaceutical preparations according to generally known processes, such as, for example, into tablets, hard gelatin capsules, dragees, solution for oral administration, injectable solution, suspensions for oral administration, emulsions and suppositories.

Apart from non-toxic and pharmaceutically acceptable inert excipients such as, for example, distilled water, glucose, lactose, starch, talc, vegetable oils, ethylene glycol, and the like, these preparations can also contain preservatives, stabilizers, wetting agents, emulsifiers, and the like.

The compositions thereby obtained generally take the form of measured doses, and can contain, depending on the conditions treated and on the patient's age and sex, from 0.1 to 100 mg of active principle. Depending on the circumstances, they may be administered orally, rectally or parenterally, at a dose of 0.1 to 100 mg from one to several times a day.

The examples which follow illustrate the invention and in no way limit it.

The NMR parameters relating to the compounds exemplified are collated in Tables I–VIII.

EXAMPLE 1

6-HYDROXY-5,6-DIHYDRO-4-OXO-4H-PYRROLO[1,2-a]THIENO[2,3-f][1,4]DIAZEPINE

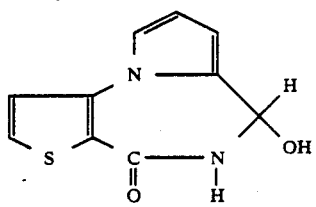

A suspension of 1.5 g (0.0068 mol) of 2-aminocarbonyl-3-(2-formyl-1-pyrrolyl-)thiophene in 30 ml of water and 0.75 ml of triethylamine is stirred at room temperature for 2 hours The precipitate formed is drained, washed with water and recrystallized in ethyl ether.

1 g of 6-hydroxy-5,6-dihydro-4-oxo-4H-pyrrolo-[1,2-a]thieno[2,3-f][1,4]diazepine is obtained in the form of yellow crystals, melting point 172° C.

Yield: 67%.

|  | Elemental analysis: | | | |
|---|---|---|---|---|
|  | C % | H % | N % | S % |
| Calculated | 54.53 | 3.66 | 12.72 | 14.56 |
| Found | 53.78 | 3.48 | 13.09 | 14.85 |

IR spectrum (KBr)

OH band at 3520 cm$^{-1}$

NH bands at 3420 and 3280 cm$^{-1}$

CO band at 1640 cm$^{-1}$ main bands at 1550, 1500, 1450, 1320, 1200, 1145, 870, 765 and 720 cm$^{-1}$.

EXAMPLE 2

6-METHOXY-5,6-DIHYDRO-4-OXO-4H-PYRROLO[1,2-a]THIENO[2,3-f][1,4]DIAZEPINE

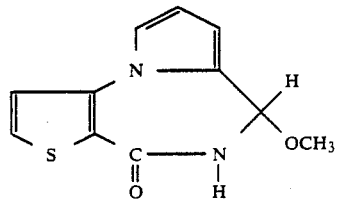

First method

A suspension of 1 g (0.0045 mol) of 2-aminocarbonyl-3-(2-formyl-1-pyrrolyl)thiophene in 30 ml of methanol is heated to reflux for one hour. The methanol is then removed under vacuum and the solid residue recrystallized in methanol.

0.97 g of 6-methoxy-5,6-dihyiro-4-oxo-4H -pyrrolo[1,2-a]thieno[2,3-f][1,4]diazepine is obtained in the form of white crystals, melting point 172° C.

Yield: 92%.

|  | Elemental analysis: | | | |
|---|---|---|---|---|
|  | C % | H % | N % | S % |
| Calculated | 56.39 | 4.30 | 11.95 | 13.68 |
| Found | 56.62 | 3.99 | 11.81 | 13.32 |

IR spectrum (KBr)

NH band at 3250 cm$^{-1}$

CH bands at 3100, 2930 and 2830 cm$^{-1}$

CO band at 1650 cm$^{-1}$ main bands at 1550, 1440, 1315, 1150, 1045, 730 and 715 cm$^{-1}$.

Second method

Using the procedure described in the first method and starting with 1 g (0.0045 mol) of 6-hydroxy-5,6-dihydro-4-oxo-4H-pyrrolo[1,2-a]thieno[2,3-f][1,4]diazepine in 30 ml of methanol, 1 g of 6-methoxy-5,6-dihydro -4-oxo-4H-pyrrolo[1,2-a]thieno[2,3-f][1,4]diazepine is obtained.

Yield: 95%.

The infrared spectrum of the compound thereby obtained is coincident with that of the compound prepared by the first method.

EXAMPLES 3-6

Using procedures similar to that described in Example 2, the following compounds were prepared: (In all cases, irrespective of the preparation method used, the infrared spectra of the compounds obtained are coincident.)

3) 6-ETHOXY-5,6-DIHYDRO-4-OXO-4H-PYRROLO[1,2-a]THIENO[2,3-f][1,4]DIAZEPINE, in the form of white crystals, melting point 148° C. (ethanol),

| | Elemental analysis: | | | |
|---|---|---|---|---|
| | C % | H % | N % | S % |
| Calculated | 58.05 | 4.87 | 11.28 | 12.91 |
| Found | 57.83 | 4.80 | 11.20 | 12.79 |

IR spectrum (KBr)

NH bands at 3260 and 3180 cm$^{-1}$
CH bands at 3060, 2970, 2930 and 2870 cm$^{-1}$
CO band at 1635 cm$^{-1}$
main bands at 1550, 1500, 1440, 1325, 1235, 1045, 960, 735 and 715 cm$^{-1}$,
from:
a) 2-aminocarbonyl-3-(2-formyl-1-pyrrolyl)thiophene and ethanol, in an 86% yield, and
b) 6-hydroxy-5,6-dihydro-4-oxo-4H-pyrrolo[1,2-a]thieno[2,3-f][1,4]diazepine and ethanol, in an 89% yield.

4) 6-PROPOXY-5,6-DIHYDRO-4-OXO-4H-PYRROLO[1,2-a]THIENO[2,3-f][1,4]DIAZEPINE, in the form of white needles, melting point 164° C. (ethyl ether),

| | Elemental analysis: | | | |
|---|---|---|---|---|
| | C % | H % | N % | S % |
| Calculated | 59.52 | 5.38 | 10.68 | 12.22 |
| Found | 59.59 | 5.33 | 10.72 | 12.08 |

IR spectrum (KBr)

NH band at 3300 cm$^{-1}$
CH bands at 3120, 2960, 2940 and 2880 cm$^{-1}$
CO band at 1645 cm$^{-1}$
CN band at 1605 cm$^{-1}$
main bands at 1500, 1450, 1325, 1150, 1060, 740 and 720 cm$^{-1}$,
from:
a) 2-aminocarbonyl-3-(2-formyl-1-pyrrolyl)thiophene and propanol, in a 75% yield, and
b) 6-hydroxy-5,6-dihydro-4-oxo-4H-pyrrolo[1,2-a]thieno[2,3-f][1,4]diazepine and propanol, in an 80% yield.

5) 6-(1-METHYLETHOXY)-5,6-DIHYDRO-4-OXO-4H-PYRROLO[1,2-a]THIENO[2,3-f][1,4]DIAZEPINE, in the form of white crystals, melting point 160° C. (isopropanol),

| | Elemental analysis: | | | |
|---|---|---|---|---|
| | C % | H % | N % | S % |
| Calculated | 59.52 | 5.37 | 10.67 | 12.22 |
| Found | 59.44 | 5.30 | 10.62 | 12.06 |

IR spectrum (KBr)

NH bands at 3260 and 3170 cm$^{-1}$
CH bands at 3100, 3050, 2960 and 2880 cm$^{-1}$
CO band at 1640 cm$^{-1}$
main bands at 1550, 1500, 1460, 1440, 1325, 1110, 1020, 805 and 720 cm$^{-1}$, from:
a) 2-aminocarbonyl-3-(2-formyl-1-pyrrolyl)thiophene and isopropanol, in a 80% yield, and
b) 6-hydroxy-5,6-dihydro-4-oxo-4H-pyrrolo[1,2-a]thieno[2,3-f][1,4]diazepine and isopropanol, in an 76% yield.

6) 6-BENZYLOXY-5,6-DIHYDRO-4-OXO-4H-PYRROLO[1,2-a]THIENO[2,3-f][1,4]DIAZEPINE, in the form of white crystals, melting point 179° C. (ethyl ether),

| | Elemental analysis: | | | |
|---|---|---|---|---|
| | C % | H % | N % | S % |
| Calculated | 65.79 | 4.55 | 9.02 | 10.33 |
| Found | 65.31 | 4.71 | 9.22 | 10.66 |

IR spectrum (KBr)

NH bands at 3270 and 3190 cm$^{-1}$
CH bands at 3060, 2940 and 2880 cm$^{-1}$
CO band at 1645 cm$^{-1}$
main bands at 1540, 1495, 1450, 1320, 1205, 1015, 795 and 735 cm$^{-1}$,
from:
a) 2-aminocarbonyl-3-(2-formyl-1-pyrrolyl)thiophene and benzyl alcohol, in a 60% yield, and
b) 6-hydroxy-5,6-dihydro-4-oxo-4H-pyrrolo[1,2-a]thieno[2,3-f][1,4]diazepine and benzyl alcohol, in a 64% yield.

EXAMPLE 7
6-METHOXYCARBONYLMETHYLMERCAPTO-5,6-DIHYDRO-4-OXO-4H-PYRROLO[1,2-a]THIENO[2,3-f][1,4]DIAZEPINE:

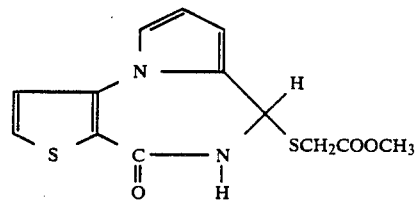

A solution of 0.7 g (0.0032 mol) of 2-aminocarbonyl-3-(2-formyl-1-pyrrolyl)thiophene in 80 ml of acetonitrile is treated with 0.3 ml (0.0035 mol) of methyl thioglycolate. The reaction mixture is stirred at room temperature for 12 hours. The acetonitrile is then removed under vacuum. The residual oil which crystallizes on addition of petroleum ether is recrystallized.

0.65 g of 6-methoxycarbonylmethylmercapto-5,6-dihydro-4-oxo-4H-pyrrolo[1,2-a]thieno[2,3-f][1,4]-diazepine is obtained in the form of white crystals, melting point 158° C. (ethyl ether).

Yield: 68%.

|  | Elemental analysis: | | | |
|---|---|---|---|---|
|  | C % | H % | N % | S % |
| Calculated | 50.64 | 3.92 | 9.08 | 20.79 |
| Found | 50.55 | 3.67 | 8.97 | 20.71 |

IR spectrum (KBr)

NH bands at 3270 and 3160 cm$^{-1}$
CH bands at 3050, 3010 and 2920 cm$^{-1}$
CO bands at 1715 cm$^{-1}$ (ester) and 1645 cm$^{-1}$ (lactam)
main bands at 1545, 1490, 1450, 1440, 1310, 1220, 1145, 755 and 720 cm$^{-1}$.

EXAMPLES 8–9

Using procedures similar to that described in Example 7, the following compounds were prepared:

8)
6-PHENYLMERCAPTO-5,6-DIHYDRO-4-OXO-4H-PYRROLO[1,2-a]THIENO[2,3-f][1,4]DIAZEPINE,
in the form of white needles, melting point 178° C. (ethyl ether),

|  | Elemental analysis: | | | |
|---|---|---|---|---|
|  | C % | H % | N % | S % |
| Calculated | 61.51 | 3.87 | 8.97 | 20.52 |
| Found | 61.70 | 3.96 | 9.10 | 20.54 |

IR spectrum (KBr)

NH bands at 3270 and 3160 cm$^{-1}$
CH bands at 3180 and 3160 cm$^{-1}$
CO band at 1645 cm$^{-1}$
main bands at 1550, 1500, 1480, 1440, 1395, 1330, 1065, 775, 720 and 690 cm$^{-1}$,
from 2-aminocarbonyl-3-(2-formyl-1-pyrrolyl)thiophene and thiophenol, in a 72% yield.

9)
6-CARBOXYETHYLMERCAPTO-5,6-DIHYDRO-4-OXO-4H-PYRROLO[1,2-a]THIENO[2,3-f][1,4]DIAZEPINE,
in the form of white crystals, melting point 190° C. (ethyl ether),

|  | Elemental analysis: | | | |
|---|---|---|---|---|
|  | C % | H % | N % | S % |
| Calculated | 50.64 | 3.92 | 9.08 | 20.79 |
| Found | 50.53 | 3.89 | 9.09 | 20.79 |

IR spectrum (KBr)

OH band at 3450 cm$^{-1}$
NH band at 3240 cm$^{-1}$
CH bands at 3150, 3020 and 2930 cm$^{-1}$
CO bands at 1700 cm$^{-1}$ (acid) and 1610 cm$^{-1}$ (lactam)
main bands at 1500, 1450, 1330, 1195, 770 and 720 cm$^{-1}$,
from 2-aminocarbonyl-3-(2-formyl-1-pyrrolyl)thiophene and 3-mercaptopropionic acid, in a 43% yield.

EXAMPLE 10

6-METHYLAMINO-5,6-DIHYDRO-4-OXO-4H-PYRROLO -[1,2-a]THIENO[2,3-f][1,4]DIAZEPINE:

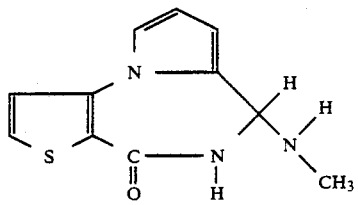

3 ml of 35% aqueous solution of methylamine are added in a single portion to a suspension of 1.1 g (0.005 mol) of 6-hydroxy-5,6-dihydro-4-oxo-4H-pyrrolo -[1,2-a]thieno[2,3-f][1,4]diazepine in 20 ml of water, and the reaction mixture is then stirred for 4 hours at room temperature The product is gradually solubilized and then reprecipitates The precipitate is drained, washed with water, dried and recrystallized. 0.7 g of 6-methylamino-5,6-dihydro-4-oxo-4H -pyrrolo[1,2-a]thieno[2,3-f][1,4]diazepine is obtained in the form of white crystals, melting point 146° C. (ethyl ether).

Yield: 60%.

|  | Elemental analysis: | | | |
|---|---|---|---|---|
|  | C % | H % | N % | S % |
| Calculated | 56.63 | 4.75 | 18.01 | 13.74 |
| Found | 56.28 | 4.51 | 17.91 | 13.18 |

IR spectrum (KBr)

NH bands at 3320, 3250 and 3180 cm$^{-1}$
CH bands at 3040, 2980 and 2900 cm$^{-1}$
CO band at 1625 cm$^{-1}$
main bands at 1550, 1495, 1440, 1320, 1100, 770 and 710 cm$^{-1}$.

EXAMPLES 11–19

Using procedures similar to that described in Example 10, the following compounds were prepared:

11) 6-ETHYLAMINO-5,6-DIHYDRO-4-OXO-4H-PYRROLO[1,2-a]THIENO[2,3-f][1,4]DIAZEPINE,
in the form of white crystals, melting point 152° C. (ethyl ether),

|  | Elemental analysis: | | | |
|---|---|---|---|---|
|  | C % | H % | N % | S % |
| Calculated | 58.28 | 5.3 | 16.99 | 12.96 |
| Found | 58.21 | 5.26 | 16.58 | 12.48 |

IR spectrum (KBr)

NH bands at 3290 and 3150 cm$^{-1}$
CH bands at 3050, 2960 and 2860 cm$^{-1}$
CO band at 1630 cm$^{-1}$
main bands at 1550, 1490, 1450, 1320, 1200, 760 and 720 cm$^{-1}$, from 6-hydroxy-5,6-dihydro-4-oxo-4H-pyrrolo[1,2-a]thieno -[2,3-f][1,4]diazepine and ethylamine, in a 72% yield.

12) 6-PROPYLAMINO-5,6-DIHYDRO-4-OXO-4H -PYRROLO[1,2-a]THIENO[2,3-f][1,4]DIAZEPINE, in the form of white crystals, melting point 130° C. (ethyl ether),

| | Elemental analysis: | | | |
|---|---|---|---|---|
| | C % | H % | N % | S % |
| Calculated | 59.75 | 5.78 | 16.08 | 12.27 |
| Found | 59.63 | 5.82 | 15.95 | 12.13 |

IR spectrum (KBr)

NH bands at 3340, 3260 and 3170 cm$^{-1}$
CH bands at 3100, 3010, 2960 and 2860 cm$^{-1}$
CO band at 1625 cm$^{-1}$
main bands at 1540, 1495, 1435, 1330, 1095 and 740 cm$^{-1}$,
from 6-hydroxy-5,6-dihydro-4-oxo-4H-pyrrolo[1,2-a]thieno -[2,3-f][1,4]diazepine and propylamine in an 85% yield.

13) 6-PYRROLIDINO-5,6-DIHYDRO-4-OXO-4H -PYRROLO[1,2-a]THIENO[2,3-f][1,4]DIAZEPINE, in the form of white crystals, melting point 191° C. (ethyl ether),

| | Elemental analysis: | | | |
|---|---|---|---|---|
| | C % | H % | N % | S % |
| Calculated | 61.52 | 5.53 | 15.37 | 11.73 |
| Found | 61.62 | 5.41 | 15.35 | 11.79 |

IR spectrum (KBr)

NH bands at 3260 and 3190 cm$^{-1}$
CH bands at 3050, 2960 and 2800 cm$^{-1}$
CO band at 1620 cm$^{-1}$
main bands at 1550, 1495, 1390, 1305, 1125, 870 and 710 cm$^{-1}$,
from 6-hydroxy-5,6-dihydro-4-oxo-4H-pyrrolo[1,2-a]thieno -[2,3-f][1,4]diazepine and pyrrolidine, in a 93% yield.

14) 6-PIPERIDINO-5,6-DIHYDRO-4-OXO-4H -PYRROLO[1,2-a]THIENO[2,3-f][1,4]DIAZEPINE, in the form of white crystals, melting point 178° C. (ethyl ether),

| | Elemental analysis: | | | |
|---|---|---|---|---|
| | C % | H % | N % | S % |
| Calculated | 62.69 | 5.96 | 14.62 | 11.16 |
| Found | 62.65 | 5.96 | 14.57 | 11.20 |

IR spectrum (KBr)

NH bands at 3260 and 3170 cm$^{-1}$
CH bands at 3050, 2940, 2860 and 2810 cm$^{-1}$
CO band at 1640 cm$^{-1}$
main bands at 1550, 1500, 1460, 1310, 1230, 1150, 980, 770, 740 and 720 cm$^{-1}$,
from 6-hydroxy-5,6-dihyiro-4-oxo-4H-pyrrolo[1,2-a]thieno -[2,3-f][1,4]diazepine and piperidine, in an 89% yield.

15) 6-MORPHOLINO-5,6-DIHYDRO-4-OXO-4H -PYRROLO[1,2-a]THIENO[2,3-f][1,4]DIAZEPINE, in the form of transparent crystals, melting point 198° C. (ethyl ether),

| | Elemental analysis: | | | |
|---|---|---|---|---|
| | C % | H % | N % | S % |
| Calculated | 58.11 | 5.22 | 14.52 | 11.08 |
| Found | 57.92 | 5.23 | 14.46 | 10.95 |

IR spectrum (KBr)

NH bands at 3270 and 3170 cm$^{-1}$
CH bands at 3050, 2950, 2930 and 2840 cm$^{-1}$
CO band at 1640 cm$^{-1}$
main bands at 1500, 1460, 1310, 1120, 990, 875 and 715 cm$^{-1}$,
from 6-hydro-xy-5,6-dihydro-4-oxo-4H-pyrrolo[1,2-a]thieno -[2,3-f][1,4]diazepine and morpholine, in a 92% yield.

16) 6-CYCLOPROPYLAMINO-5,6-DIHYDRO-4-OXO-4H -PYRROLO[1,2-a]THIENO[2,3-f][1,4]DIAZEPINE, in the form of white crystals, melting point 185° C. (ethyl ether),

| | Elemental analysis: | | | |
|---|---|---|---|---|
| | C % | H % | N % | S % |
| Calculated | 60.21 | 5.05 | 16.20 | 12.36 |
| Found | 60.67 | 5.30 | 15.87 | 11.90 |

IR spectrum (KBr)

NH bands at 3340, 3260 and 3150 cm$^{-1}$
CH bands at 3020, 2960 and 2880 cm$^{-1}$
CO band at 1630 cm$^{-1}$
main bands at 1540, 1490, 1460, 1370, 1290, 1120, 870, 790, 735 and 720 cm$^{-1}$,
from 6-hydroxy-5,6-dihydro-4-oxo-4H--pyrrolo[1,2-a]thieno -[2,3-f][1,4]diazepine and cyclopropylamine, in an 86% yield.

17) 6-(4-ETHOXYCARBONYLPIPERAZINO)-5,6-DIHYDRO -4-OXO-4H-PYRROLO[1,2-a]THIENO[2,3-f][1,4]DIAZEPINE, in the form of white crystals, melting point 180° C. (ethyl ether),

| | Elemental analysis: | | | |
|---|---|---|---|---|
| | C % | H % | N % | S % |
| Calculated | 56.65 | 5.59 | 15.54 | 8.89 |
| Found | 56.76 | 5.48 | 15.47 | 8.78 |

IR spectrum (KBr)

NH bands at 2260 and 3160 cm$^{-1}$
CH bands at 3110, 2980 and 2810 cm$^{-1}$
CO bands at 1690 cm$^{-1}$ (ester) and 1640 cm$^{-1}$ (lactam)
main bands at 1515, 1495, 1250, 1225, 985, 870, 770 and 710 cm$^{-1}$, from 6-hydroxy-5,6-dihydro-4-oxo-4H-pyrrolo[1,2-a]thieno -[2,3-f][1,4]diazepine and 4-ethoxycarbonylpiperazine, in an 80% yield.

18)
6-(4-PHENYLPIPERAZINO)-5,6-DIHYDRO-4-OXO-4H
-PYRROLO[1,2-a]THIENO[2,3-f][1,4]DIAZEPINE,
in the form of white crystals, melting point 150° C. (ethyl ether),

|  | Elemental analysis: | | | |
| --- | --- | --- | --- | --- |
|  | C % | H % | N % | S % |
| Calculated | 65.91 | 5.53 | 15.37 | 8.8 |
| Found | 65.31 | 5.59 | 14.98 | 8.52 |

IR spectrum (KBr)

NH bands at 3300 and 3220 cm$^{-1}$
CH bands at 3120, 3090, 2980, 2930 and 2820 cm$^{-1}$
CO bands at 1495, 1445, 1305, 1050, 770 and 730 cm$^{-1}$,
from 6-hydroxy-5,6-dihydro-4-oxo-4H-pyrrolo[1,2-a]thieno -[2,3-f][1,4]diazepine and N-phenylpiperazine, in a 76% yield.

19) 6-BENZYLAMINO-5,6-DIHYDRO-4-OXO-4H
-PYRROLO[1,2-a]THIENO[2,3-f][1,4]DIAZEPINE,
in the form of white crystals, melting point 161° C. (ethyl ether),

|  | Elemental analysis: | | | |
| --- | --- | --- | --- | --- |
|  | C % | H % | N % | S % |
| Calculated | 66 | 4.89 | 13.58 | 10.36 |
| Found | 65.85 | 5.56 | 13.27 | 10.27 |

IR spectrum (KBr)

NH bands at 3340 and 3200 cm$^{-1}$
CH bands at 3080 and 2900 cm$^{-1}$
main bands at 1550, 1500, 1460, 1130 and 720 cm$^{-1}$
from 6-hydroxy-5,6-dihydro-4--oxo-4H-pyrrolo[1,2-a]thieno -[2,3-f][1,4]diazepine and benzylamine, in a 72% yield.

EXAMPLE 20

5,6-DIHYDRO-4-OXO-4H-PYRROLO[1,2-a]THIENO[2,3-f][1,4]DIAZEPINE:

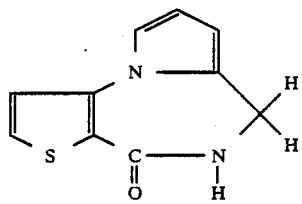

1 g (0.0028 mol) of sodium borohydride is added in small portions to a solution of 2 g (0.007 mol) of 6-piperidino-5,6-dihydro-4-oxo-4H-pyrrolo[1,2-a]thieno -[2,3-f][1,4]diazepine in 120 ml of methanol, and the reaction mixture is stirred at room temperature for 15 minutes and then heated to reflux for 30 minutes. The methanol is then removed under vacuum and the solid residue ground in 200 ml of water. The precipitate is drained, washed with water, dried and recrystallized. 1.2 g of 5,6-dihydro-4-oxo-4H-pyrrolo[1,2-a]- thieno[2,3-f][1,4]diazepine are obtained in the form of white crystals, melting point 191° C. (ethyl ether).
Yield: 84%.

|  | Elemental analysis: | | | |
| --- | --- | --- | --- | --- |
|  | C % | H % | N % | S % |
| Calculated | 58.81 | 3.95 | 13.72 | 15.70 |
| Found | 58.70 | 3.97 | 13.64 | 15.54 |

IR spectrum (KBr)

NH bands at 3230 and 3160 cm$^{-1}$
CH bands at 3110, 3030 and 2890 cm$^{-1}$
CO band at 1635 cm$^{-1}$
main bands at 1540, 1490, 1450, 1330, 1195, 790, 755 and 730 cm$^{-1}$

EXAMPLE 21

6-ACETONYL-5,6-DIHYDRO-4-OXO-4H-PYRROLO[1,2-a]-THIENO[2,3-f][1,4]DIAZEPINE:

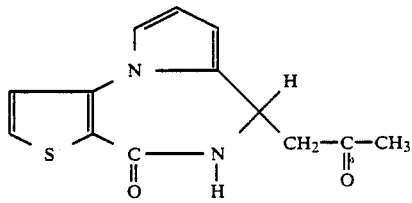

1 g (0.0045 mol) of 6-hydroxy-5,6-dihydro-4-oxo -4H-pyrrol-o[1,2-a]thieno[2,3-f][1,4]diazepine is added in a single portion to an emulsion of 20 ml of acetone in 10 ml of 10N sodium hydroxide, and the reaction mixture is stirred vigorously at room temperature for 3 hours. The acetone is then removed under vacuum and 100 ml of water are poured onto the liquid residue. The yellow precipitate obtained is drained, washed with water and recrystallized. 0.7 g of 6-acetonyl-5,6-dihydro-4-oxo-4H -pyrrolo[1,2-a]thieno[2,3-f][1,4]diazepine is obtained in the form of white crystals, melting point 268° C. (isopropanol).
Yield: 60%.

|  | Elemental analysis: | | | |
| --- | --- | --- | --- | --- |
|  | C % | H % | N % | S % |
| Calculated | 59.98 | 4.65 | 10.76 | 12.32 |
| Found | 59.78 | 4.72 | 10.64 | 11.96 |

IR spectrum (KBr)

NH bands at 3270 and 3150 cm$^{-1}$
CH bands at 3040, 2980 and 2880 cm$^{-1}$
CO bands at 1700 cm$^{-1}$ (ketone) and 1640 cm$^{-1}$ (lactam)
main bands at 1540, 1490, 1455, 1380, 1140, 765 and 720 cm$^{-1}$ EXAMPLES 22 to 24

Using procedures similar to that described in Example 21, the following compounds were prepared:

22)
6-(3-METHYL-2-OXO-1-BUTYL)-5,6-DIHYDRO-4-OXO -4H-PYRROLO[1,2-a]THIENO[2,3-f][1,4]DIAZE-PINE, in the form of white crystals, melting point 172° C. (ethyl ether), Elemental analysis:

|  | C % | H % | N % | S % |
|---|---|---|---|---|
| Calculated | 62.48 | 5.59 | 9.71 | 11.12 |
| Found | 62.39 | 5.44 | 9.88 | 10.89 |

IR spectrum (KBr)

NH bands at 3290 and 3130 cm$^{-1}$
CH bands at 3140, 3100, 3000 and 2950 cm$^{-1}$
C=O bands at 1715 cm$^{-1}$ (ether) and 1645 cm$^{-1}$ (lactam)
main bands at 1500, 1340, 1170, 960, 870 and 745 cm$^{-1}$,
from 6-hydroxy-5,6-dihydro-4-oxo-4H-pyrrolo[1,2-a]thieno -[2,3-f][1,4]diazepine and isopropyl methyl ketone, in a yield.

23)
6-PHENACYL-5,6-DIHYDRO-4-OXO-4H-PYR-ROLO[1,2-a]THIENO[2,3-f][1,4]DIAZEPINE, in the form of white crystals, melting point 214° C. (ethyl ether), Elemental analysis:

|  | C % | H % | N % | S % |
|---|---|---|---|---|
| Calculated | 67.06 | 4.38 | 8.69 | 9.94 |
| Found | 66.99 | 4.44 | 8.69 | 10.20 |

IR spectrum (KBr)

NH bands at 3280 and 3170 cm$^{-1}$
CH bands at 2960 and 2830 cm$^{-1}$
C=O bands at 1690 cm$^{-1}$ (ketone) and 1655 cm$^{-1}$ (lactam)
main bands at 1490, 1450, 1140, 770 and 695 cm$^{-1}$,
from 6-hydroxy-5,6-dihyiro-4-oxo-4H-pyrrolo[1,2-a]thieno -[2,3-f][1,4]diazepine and acetophenone, in a 15% yield.

24)
6-(4-FLUOROPHENACYL)-5,6-DIHYDRO-4-OXO-4H -PYRROLO[1,2-a]THIENO[2,3-f][1,4]DIAZEPINE, in the form of yellow crystals, melting point 250° C. (ethyl ether), Elemental analysis:

|  | C % | H % | N % | S % | F % |
|---|---|---|---|---|---|
| Calculated | 63.51 | 3.84 | 8.23 | 9.41 | 5.58 |
| Found | 65.98 | 3.65 | 8.15 | 9.62 | 5.39 |

IR spectrum (KBr)

NH bands at 3280 and 3180 cm$^{-1}$
CH bands at 3000, 2900 and 2840 cm$^{-1}$
C=O bands at 1670 cm$^{-1}$ (ether) and 1630 cm$^{-1}$ (lactam)
main bands at 1480, 1435, 1140, 1110, 760 and 710 cm$^{-1}$,
from 6-hydroxy-5,6-dihydro-4-oxo-4H-pyrrolo[1,2-a]thieno -[2,3-f][1,4]diazepine and para-fluoroacetophenone, in a 16% yield.

EXAMPLE 25

6-(2-HYDROXYPROPYL)5,6-DIHYDRO-4-OXO-4H -PYRROLO[1,2-a]THIENO[2,3-f][1,4]DIAZEPINE:

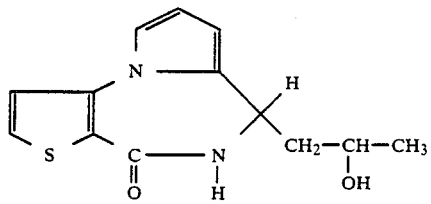

0.58 g (0.0152 mol) of sodium borohydride is added to a solution of 1 g (0.0038 mol) of 6-acetonyl -5,6-dihydro-4-oxo-4H-pyrrolo[1,2-a]thieno[2,3-f][1,4]-diazepine in 250 ml of methanol, and the reaction mixture is then stirred at room temperature for 3 hours. The methanol is then removed under vacuum and the solid residue is ground in 200 ml of water. The precipitate obtained is drained, washed with water, dried and recrystallized.

0.8 g of 6-(2-hydroxypropyl)-5,6-dihydro-4-oxo -4H-pyrrolo[1,2-a]thieno[2,3-f][1,4]diazepine is obtained in the form of white crystals, melting point 170° C. (ethyl ether).

Yield: 80%.

Elemental analysis:

|  | C % | H % | N % | S % |
|---|---|---|---|---|
| Calculated | 59.52 | 5.38 | 10.68 | 12.22 |
| Found | 59.55 | 5.18 | 10.58 | 12.06 |

IR spectrum (KBr)

OH band at 3420 cm$^{-1}$
NH bands at 3360 and 3180 cm$^{-1}$
CH bands at 3030, 2970 and 2860 cm$^{-1}$
CO band at 1625 cm$^{-1}$
main bands at 1485, 1440, 870, 765 and 710 cm$^{-1}$

EXAMPLE 26

6-[(ETHOXYCARBONYL(CYANO)METHYL]-5,6-DIHYDRO-4-OXO-4H-PYRROLO[1,2-a]THIENO[2,3-f][1,4]DIAZEPINE

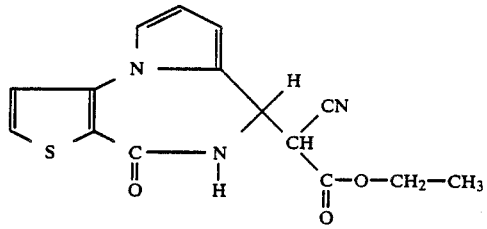

2 ml of ethyl cyanoacetate and 0.5 ml of triethylamine are added to a solution of 1 g (0.0045 mol) of 6-hydroxy-5,6-dihydro-4-oxo-4H-pyrrolo[1,2-a]thieno[2,3-f][1,4]diazepine in 100 ml of acetonitrile, and the reaction mixture is then stirred at room temperature for 12 hours. The acetonitrile is then removed under vacuum. The residue obtained is ground in 200 ml of water. The precipitate obtained is drained, washed with water, dried and recrystallized.

0.7 g of 6-[ethoxycarbonyl(cyano)methyl]-5,6-dihydro-4-oxo-4H-pyrrolo[1,2-a]thieno[2,3-f][1,4]diazepine is obtained in the form of yellow crystals, melting point 195° C. (ethyl ether).

Yield: 49%.

|  | Elemental analysis: | | | |
|---|---|---|---|---|
|  | C % | H % | N % | S % |
| Calculated | 57.13 | 4.16 | 13.33 | 10.17 |
| Found | 57.07 | 4.24 | 13.28 | 10.06 |

IR spectrum (KBr)

NH bands at 3340, 3280 and 3180 cm$^{-1}$
CH bands at 3120 and 2990 cm$^{-1}$
C≡N band at 2230 cm$^{-1}$
CO bands at 1720 cm$^{-1}$ (ether) and 1670 cm$^{-1}$ (lactam)
main bands at 1595, 1465, 1435, 1365, 1300, 1240, 1090, 875 and 750 cm$^{-1}$

EXAMPLE 27

6-[(METHOXYCARBONYL(CYANO)METHYL]-5,6-DIHYDRO-4-OXO-4H-PYRROLO[1,2-a]THIENO[2,3-f][1,4]DIAZEPINE, prepared as described in Example 26 from 6-hydroxy-5,6-dihydro-4-oxo-4H-pyrrolo[1,2-a]thieno[2,3-f][1,4]diazepine and methyl cyanoacetate.

EXAMPLE 28

6-[1-(ETHOXYCARBONYL)ACETONYL]-5,6-DIHYDRO-4-OXO-4H-PYRROLO[1,2-a]THIENO[2,3-f][1,4]DIAZEPINE:

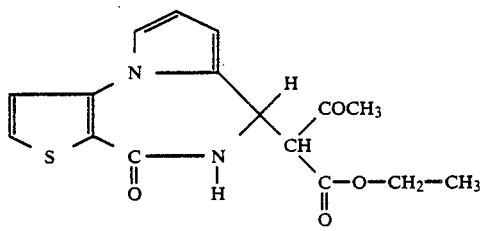

Using the procedure described in Example 26, starting with 1 g of 6-hydroxy-5,6-dihydro-4-oxo-4H-pyrrolo[1,2-a]thieno[2,3-f][1,4]diazepine and 2 ml of ethyl acetoacetate, 0.7 g of 6-[1-(ethoxycarbonyl)-acetonyl]-5,6-dihydro-4-oxo-4H-pyrrolo[1,2-a]thieno -[2,3-f][1,4]diazepine was obtained in the form of white crystals, melting point 196° C. (ethyl ether).

Yield: 47%.

|  | Elemental analysis: | | | |
|---|---|---|---|---|
|  | C % | H % | N % | S % |
| Calculated | 57.82 | 4.85 | 8.43 | 9.65 |
| Found | 57.75 | 4.78 | 8.37 | 9.85 |

IR spectrum (KBr)

NH bands at 3270 and 3200 cm$^{-1}$
CH bands at 3120, 2940 and 2870 cm$^{-1}$
CO bands at 1710 and 1635 cm$^{-1}$ main bands at 1545, 1495, 1300, 1255, 1030 and 790 cm$^{-1}$

EXAMPLE 29

5,6-DIHYDRO-4H-PYRROLO[1,2-a]THIENO[2,3-f][1,4]-DIAZEPINE AND ITS HYDROCHLORIDE:

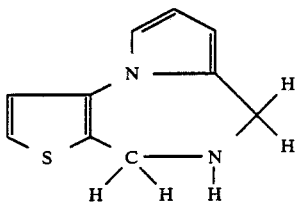

A solution of 5.3 g (0.024 mol) of 6-hydroxy-5,6-dihydro-4-oxo-4H-pyrrolo[1,2-a]thieno[2,3-f][1,4]diazepine in 400 ml of dichloromethane is added in small portions to a suspension of 3.66 g (0.096 mol) of lithium aluminum hydride in 20 ml of ethyl ether. The reaction mixture is stirred at room temperature for 30 minutes and then heated to reflux for 6 hours. After cooling, the solution obtained is poured onto 250 g of ice. The emulsion formed is drained and the organic phase is then separated after settling has taken place. The aqueous phase is extracted with 200 ml of dichloromethane. The organic phases are combined, dried over calcium chloride, purified with animal charcoal and evaporated under vacuum. The residual oil is dissolved in 300 ml of ethyl ether and a stream of gaseous HCl is bubbled into this ethereal solution for 15 seconds. The precipitate is drained, washed with ether and recrystallized. 3.2 g of 5,6-dihydro-4H-pyrrolo[1,2-a]thieno -[2,3-f][1,4]diazepine are thereby obtained in the form of beige crystals, melting point 260° C. (isopropanol).

Yield: 59%.

|  | Elemental analysis: | | | |
|---|---|---|---|---|
|  | C % | H % | N % | Cl % |
| Calculated | 52.98 | 4.89 | 12.36 | 15.64 |
| Found | 53.20 | 4.98 | 13.93 | 15.46 |

IR spectrum (KBr)

CH bands at 3100 and 3080 cm$^{-1}$
broad band (NH$_2$+Cl$^-$) from 2900 to 2470 cm$^{-1}$
main bands at 1565, 1550, 1480, 1445, 1296, 1190, 1066, 740 and 720 cm$^{-1}$.

EXAMPLE 30

5-(p-TOLYLSULFONYL)-5,6-DIHYDRO-4H-PYRROLO -[1,2-a]THIENO[2,3-f][1,4]DIAZEPINE:

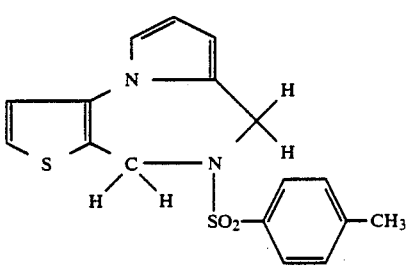

An excess of para-toluenesulfonyl chloride is added to a solution of 1 g (0.0053 mol) of 5,6-dihydro -4H-pyrrolo[1,2-a]thieno[2,3-f][1,4]diazepine in 10 ml of pyridine, and the reaction mixture is then stirred at room temperature for one hour. The pyridine is then removed under reduced pressure and the oil residue obtained is ground in 100 ml of water. The emulsion formed is extracted with 3 times 100 ml of ethyl ether. The organic phases are separated after settling has taken place, combined, dried, washed with acidulated water, dried over magnesium sulfate and evaporated under vacuum. The solid residue is recrystallized. 0.4 g of 5-(p-tolylsulfonyl)-5,6-dihydro-4H -pyrrolo[1,2-a]thieno[2,3-f][1,4]diazepine is thereby obtained in the form of yellow crystals, melting point 165° C. (ethyl ether).

Yield: 22%.

|  | Elemental analysis: | | | |
| --- | --- | --- | --- | --- |
|  | C % | H % | N % | S % |
| Calculated | 59.28 | 4.68 | 8.13 | 18.62 |
| Found | 59.21 | 4.72 | 8.05 | 18.44 |

IR spectrum (KBr)

CH bands at 3100 and 2830 cm$^{-1}$ main bands at 1580, 1490, 1440, 1355, 1165, 1090, 730 and 660 cm$^{-1}$

EXAMPLE 31

5-ACETYL-5,6-DIHYDRO-4-OXO-4H-PYRROLO[1,2-a]-THIENO[2,3-f][1,4]DIAZEPINE:

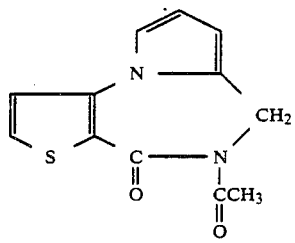

A suspension of 0.5 g of 5,6-dihydro-4-oxo-4H -pyrrolo[1,2-a]thieno[2,3-f][1,4]diazepine (Example 20) in 20 ml of acetic anhydride is heated to reflux for 2 hours. The acetic anhydride is then removed under vacuum. The oil residue is ground in 100 ml of water and the emulsion obtained extracted with ethyl ether. The ether phases are dried over magnesium sulfate and concentrated under reduced pressure The residual oil which crystallizes on addition of petroleum ether is recrystallized.

0.4 g (66%) of 5-acetyl-5,6-dihyiro-4-oxo-4H -pyrrolo[1,2-a]thieno[2,3-f][1,4]diazepine is thereby obtained in the form of yellow crystals, melting point 157° C. (ethyl ether).

|  | Elemental analysis: | | | |
| --- | --- | --- | --- | --- |
|  | C % | H % | N % | S % |
| Calculated | 58.48 | 4.06 | 5.69 | 12.99 |
| Found | 58.48 | 5.72 | 5.72 | 13.05 |

IR spectrum (KBr)

CH bands at 3150, 3120 and 3100 cm$^{-1}$
C=O bands at 1695 and 1660 cm$^{-1}$ main bands at 1540, 1490, 1430, 1345, 1220, 1200, 1150, 770 and 725 cm$^{-1}$.

EXAMPLE 32

5-(N-PHENYLCARBAMOYL)-5,6-DIHYDRO-4-OXO-4H -PYRROLO[1,2-a]THIENO[2,3-f][1,4]DIAZEPINE:

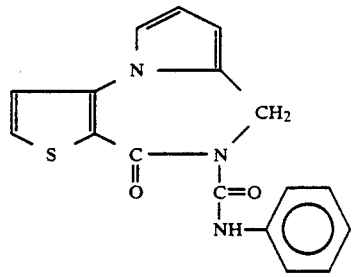

A solution of 1 g of 5,6-dihydro-4-oxo-4H -pyrrolo[1,2-a]thieno[2,3-f][1,4]diazepine (Example 20), 0.5 ml of phenyl isocyanate and 1.36 ml of triethylamine in 200 ml of toluene is heated to reflux for 2 hours. The reaction medium is then concentrated under reduced pressure and thereafter taken up with water and extracted with ethyl ether.

The ether phases are dried and then concentrated under reduced pressure.

1 g (63%) of 5-(N-phenylcarbamoyl)-5,6-dihydro -4-oxo-4H-pyrrolo[1,2-a]thieno[2,3-f][1,4]diazepine is obtained in the form of white crystals, melting point 176° C. (ethyl ether).

|  | Elemental analysis: | | | |
| --- | --- | --- | --- | --- |
|  | C % | H % | N % | S % |
| Calculated | 63.14 | 4.05 | 12.99 | 9.91 |
| Found | 63.07 | 4.08 | 13.07 | 9.92 |

IR spectrum (KBr)

NH bands at 3260 and 3220 cm$^{-1}$
CH band at 3120 cm$^{-1}$
C=O band at 1710 cm$^{-1}$
main bands at 1590, 1550, 1490, 1430, 1195, 770 and 715 cm$^{-1}$

EXAMPLE 33

5-(N-PROPYLCARBAMOYL)-5,6-DIHYDRO-4-OXO-4H -PYRROLO[1,2-a]THIENO[2,3-f][1,4]DIAZEPINE:

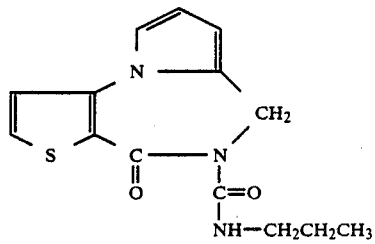

The procedure is as for Example 32, replacing phenyl isocyanate by n propyl isocyanate.

5-(N-Propylcarbamoyl)-5,6-dihydro-4-oxo-4H -pyrrolo[1,2-a]thieno[2,3-f][1,4]diazepine is obtained in the form of white crystals, melting point 120° C. (ethyl ether), in a 63% yield.

| | Elemental analysis: | | | |
|---|---|---|---|---|
| | C % | H % | N % | S % |
| Calculated | 58.11 | 5.22 | 14.52 | 11.08 |
| Found | 58.15 | 5.19 | 14.48 | 11.16 |

IR spectrum (KBr)

NH band at 3290 cm$^{-1}$
CH bands at 3070, 3030, 2970 and 2880 cm$^{-1}$
C=O bands at 1690 and 1625 cm$^{-1}$
main bands at 1485, 1430, 1380, 1330, 1200, 1210, 775 and 700 cm$^{-1}$.

The NMR parameters relating to the compounds which are the subject of Examples 1 to 33 are collated in the tables below.

TABLE I

NMR parameters relating to the compounds of Examples 1 to 6, corresponding to the formulae Ia and Ib combined in the following formula:

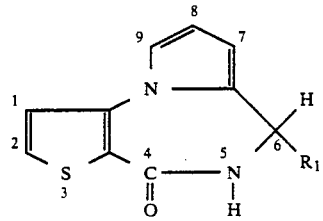

| Example No. | $R_1$ | Solvent | $H_1$ | $H_2$ | $H_7$ | $H_8$ | $H_9$ | NH | $H_6$ | Other protons |
|---|---|---|---|---|---|---|---|---|---|---|
| 1 | OH | DMSO | 7.21 | 7.21 | 6.25 | 6.25 | 7.17 | 8.59 | 5.59 | OH: 6.25 |
| 2 | OCH$_3$ | CDCl$_3$ | 7.20 | 7.56 | 6.30 | 6.30 | 7.10 | 7.47 | 5.35 | CH$_3$: 3.30 |
| 3 | OCH$_2$CH$_3$ | CDCl$_3$ | 7.18 | 7.57 | 6.29 | 6.29 | 7.08 | 7.43 | 5.46 | CH$_2$: CH: 3.70 |
| | | | | | | | | | | CH: 3.46 |
| | | | | | | | | | | CH$_3$: 1.08 |
| 4 | OCH$_2$CH$_2$CH$_3$ | CDCl$_3$ | 7.17 | 7.56 | 6.28 | 6.28 | 7.07 | 7.9 | 5.48 | CH$_2$: 3.52 |
| | | | | | | | | | | 3.34 |
| | | | | | | | | | | CH$_2$: 1.45 |
| | | | | | | | | | | CH$_3$: 0.71 |
| 5 | OCH(CH$_3$)CH$_3$ | CDCl$_3$ | 7.17 | 7.56 | 6.30 | 6.25 | 7.07 | 7.38 | 5.56 | CH: 3.81 |
| | | | | | | | | | | 2CH$_3$: 1.07 |
| 6 | OCH$_2$C$_6$H$_5$ | CDCl$_3$ | 7.17 | 7.58 | 6.29 | 6.22 | 7.08 | 7.42 | 5.47 | CH$_2$: 4.52 |
| | | | | | | | | | | C$_6$H$_5$: 5.24 |

TABLE II

NMR parameters relating to the compounds of Examples 7 to 9 of formula Ic:

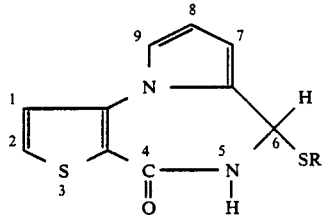

| Example No. | R | Solvent | $H_1$ | $H_2$ | $H_7$ | $H_8$ | $H_9$ | $H_6$ | NH | Other protons |
|---|---|---|---|---|---|---|---|---|---|---|
| 7 | CH$_2$COOCH$_3$ | CDCl$_3$ | 7.18 | 7.62 | 6.26 | 6.30 | 7.10 | 5.99 | 6.94 | CH: CH: 3.34 |
| | | | | | | | | | | CH: 3.04 |
| | | | | | | | | | | CH$_3$: 3.77 |
| 8 | C$_6$H$_5$ | DMSO | 7.50 | 7.94 | 6.28 | 6.28 | 7.42 | 5.78 | 9.13 | C$_6$H$_5$: 7.31 and |
| | | | | | | | | | | 7.32 |
| 9 | CH$_2$CH$_2$COOH | CDCl$_3$ | 7.21 | 7.65 | 6.14 | 6.24 | 7.09 | 5.79 | 6.75 | OH: 12.19 |
| | | | | | | | | | | CH$_2$: 2.60 |
| | | | | | | | | | | CH$_2$: 2.43 |

TABLE III

NMR parameters relating to the compounds of Examples 10 to 18 of formula Id:

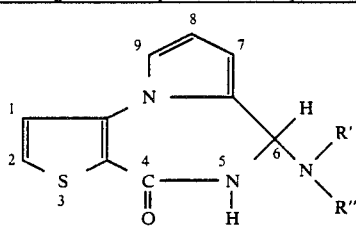

| Example No. | R' | R'' | Solvent | $H_1$ | $H_2$ | $H_7$ | $H_8$ | $H_9$ | NH | $H_6$ | Other protons |
|---|---|---|---|---|---|---|---|---|---|---|---|
| 10 | H | $CH_3$ | DMSO | 7.59 | 7.84 | 6.21 | 6.21 | 7.32 | 8.63 | 4.86 | $CH_3$: 2.20 |
| 11 | H | $CH_2CH_3$ | $CDCl_3$ | 7.17 | 7.59 | 6.18 | 6.31 | 7.03 | 6.71 | 5.15 | NH: 1.68<br>$CH_2$: CH: 2.87<br>CH: 2.71<br>$CH_3$: 1.09 |
| 12 | H | $CH_2CH_2CH_3$ | $CDCl_3$ | 7.16 | 7.58 | 6.18 | 6.31 | 7.03 | 6.67 | 5.15 | NH: 1.66<br>$CH_2$: 2.68 and 1.47<br>$CH_3$: 0.87 |
| 13 |  | (cyclopentyl) | $CDCl_3$ | 7.16 | 7.52 | 6.18 | 6.27 | 7.03 | 6.72 | 4.61 | $CH_2$: 2.63; 2.27<br>$2CH_2$: 1.63 |
| 14 |  | (cyclohexyl) | $CDCl_3$ | 7.13 | 7.5 | 6.17 | 6.28 | 7.02 | 7.36 | 4.64 | $CH_2$: 2.56 and 2.15<br>$3CH_2$: 1.35 |
| 15 |  | (tetrahydropyranyl-O) | $CDCl_3$ | 7.14 | 7.54 | 6.22 | 6.29 | 7.06 | 7.11 | 4.56 | $2CH_2$: 3.47<br>$CH_2$: 2.56 and 2.10 |
| 16 | H | $\begin{array}{c}CH_2\\CH\phantom{xx}\\CH_2\end{array}$ (cyclopropyl) | DMSO | 7.42 | 7.84 | 6.20 | 6.20 | 7.30 | 8.67 | 5.04 | NH: 2.83<br>CH: 2.09<br>$2CH_2$: 0.26 |
| 17 |  | (piperidyl-$NCOOC_2H_5$) | $CDCl_3$ | 7.14 | 7.53 | 6.21 | 6.30 | 7.06 | 7.23 | 4.60 | $CH_2$: 4.07; 2.48 and 2.06<br>$2CH_2$: 3.24 |
| 18 |  | (piperidyl-$NC_6H_5$) | DMSO | 7.14 | 7.50 | 6.25 | 6.30 | 7.13 | 9.01 | 5.64 | $2CH_2$: 3.02<br>$2CH_2$: 2.83<br>$C_6H_5$: 7.26; 6.84 |
| 19 | H | $CH_2$-$C_6H_5$ | DMSO | 7.46 | 7.88 | 6.16 | 6.25 | 7.35 | 8.80 | 4.99 | NH: 2.83<br>$CH_2$: 3.70<br>$C_6H_5$: 7.44; 7.35 |

TABLE IV

NMR parameters relating to the compound of Example 20 of formula Ie:

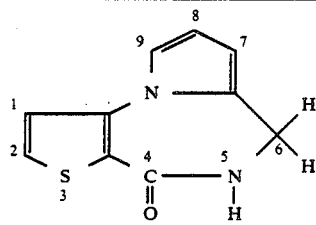

| Example No. | Solvent | $H_1$ | $H_2$ | $H_7$ | $H_8$ | $H_9$ | $CH_{2\,6}$ | Other protons |
|---|---|---|---|---|---|---|---|---|
| 20 | $CDCl_3$ | 7.16 | 7.60 | 6.12 | 6.29 | 7.01 | 4.32 | NH: 6.9 |

TABLE V

NMR parameters relating to the compounds of Examples 21 to 28 of formulae If to Ii combined in the following formula:

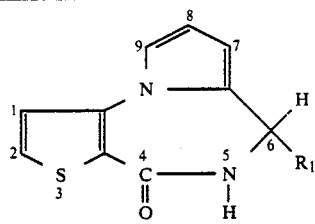

| Example No. | $R_1$ | Solvent | $H_1$ | $H_2$ | $H_7$ | $H_8$ | $H_9$ | NH | $H_6$ | Other protons |
|---|---|---|---|---|---|---|---|---|---|---|
| 21 | —CH$_2$COCH$_3$ | DMSO | 7.45 | 7.96 | 6.08 | 6.24 | 7.30 | 8.34 | 3.68 | CH$_2$: 3.16<br>CH$_3$: 2.17 |
| 22 | —CH$_2$C(O)—CH(CH$_3$)$_2$ | CDCl$_3$ | 7.86 | 7.41 | 6.06 | 6.23 | 7.27 | 8.26 | 4.6 | CH$_2$: 3.12<br>CH: 3.12<br>2 CH$_2$: 1.12 |
| 23 | —CH$_2$—C(O)—C$_6$H$_5$ | DMSO | 7.89 | 7.42 | 6.15 | 6.15 | 7.25 | 8.35 | 4.8 | CH$_2$: 3.35<br>C$_6$H$_5$: 7.94 and 7.42 |
| 24 | —CH$_2$—C(O)—C$_6$H$_4$—F | DMSO | 7.82 | 7.39 | 6.12 | 6.25 | 7.26 | 8.61 | 4.78 | CH$_2$: 3.39<br>C$_6$H$_5$: 7.12 and 7.04 |
| 25 | —CH$_2$CHOHCH$_3$ | CDCl$_3$ | 7.14 | 7.58 | 6.08 | 6.30 | 7.01 | 7.69 | 4.70 | CH: 4.24<br>CH$_2$: 2.18<br>CH$_3$: 1.30 |
| 26 | —CH(CO$_2$CH$_2$CH$_3$)(CN) | CDCl$_3$ | 7.69 | 7.69 | 7.20 | 7.20 | 7.69 | 7.69 | 5.40 | CH$_2$: 4.28<br>CH: 5.04<br>CH$_3$: 1.38 |
| 27 | —CH(CO$_2$CH$_3$)(CN) | DMSO | 7.66 | 7.92 | 6.24 | 6.24 | 7.66 | 7.66 | 6.64 | CH$_3$: 3.75 |
| 28 | —CH(COCH$_3$)(COOCH$_2$CH$_3$) | CDCl$_3$ | 7.20 | 7.65 | 6.11 | 6.28 | 7.04 | 6.62 | 5.16 | CH$_2$: 4.25<br>CH: 4.13<br>CH$_3$: 1.29<br>CH$_3$: 1.91 |

TABLE VI

Example 25:
Solvent: DMSO

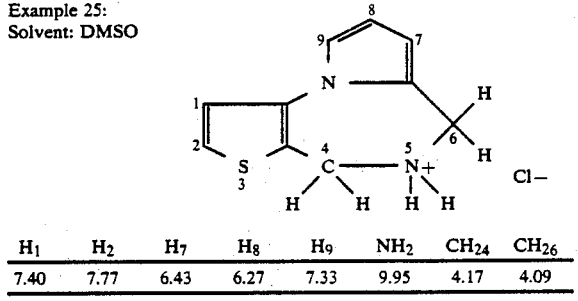

| $H_1$ | $H_2$ | $H_7$ | $H_8$ | $H_9$ | NH$_2$ | CH$_{24}$ | CH$_{26}$ |
|---|---|---|---|---|---|---|---|
| 7.40 | 7.77 | 6.43 | 6.27 | 7.33 | 9.95 | 4.17 | 4.09 |

TABLE VII

Example 26:
Solvent: CDCl$_3$

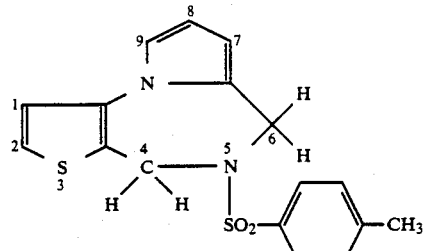

| $H_1$ | $H_2$ | $H_7$ | $H_8$ | $H_9$ | CH$_{24}$ | CH$_{26}$ | Other protons |
|---|---|---|---|---|---|---|---|
| 6.98 | 7.19 | 6.14 | 6.14 | 6.82 | 4.47 | 4.39 | C$_6$H$_4$: 7.65 and 7.23<br>CH$_3$: 2.38 |

TABLE VIII

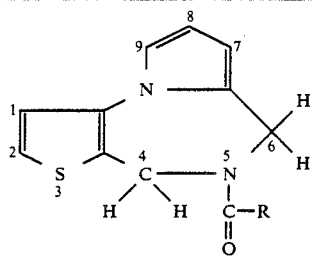

| Example No. | R | Solvent | H₁ | H₂ | H₇ | H₈ | H₉ | H₆ | Other protons |
|---|---|---|---|---|---|---|---|---|---|
| 31 | —CH₃ | DMSO | 7.56 | 8.19 | 6.26 | 6.26 | 7.43 | 5.82 | CH₃: 2.36 |
| 32 | —NH—C₆H₅ | DMSO | 7.56 | 8.21 | 6.32 | 6.32 | 7.52 | 5.79 | C₆H₅: 7.55 and 7.36 |
| 33 | —NH—CH₂CH₂CH₃ | DMSO | 7.52 | 8.14 | 6.24 | 6.30 | 7.40 | 4.90 | NH: 8.79 CH₂: 3.17 and 1.48 CH₃: 0.86 |

We claim:

1. A compound selected from a pyrrolo[1,2-a]thieno[2,3-f][1,4]diazepine of general formula (I):

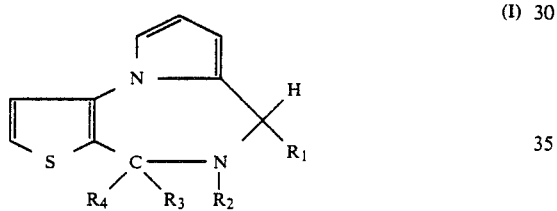

in which:
$R_1$ represents:
 hydrogen
 hydroxyl
 a radical of the formula:

—OR₅ or —SR₅ in which $R_5$ represents:
 alkyl containing 1 to 5 carbon atoms, optionally substituted with phenyl or with a group of formula —COOB in which B represents hydrogen or alkyl radical containing 1 to 5 carbon atoms, or
 phenyl, naphthyl, or pyrridyl
 a radical of the formula:

—CH₂—C(=O)—R₆ or —CH₂—CH(OH)—R₆ in which $R_6$ represents:
 alkyl having 1 to 5 carbon atoms,
 phenyl, naphthyl, pyrridinyl, thienyl, or optionally substituted with halogen, alkoxy having 1 to 3 carbon atoms, or trifluoromethyl,
 phenylalkyl having 7 to 9 carbon atoms optionally substituted on the aromatic ring with halogen, alkoxy having 1 to 3 carbon atoms, or trifluoromethyl a radical of formula:

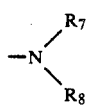

in which:
$R_7$ and $R_8$, which may be identical or different, each represent a hydrogen, alkyl containing 1 to 5 carbon atoms or cycloalkyl containing 3 to 5 carbon atoms, phenyl or naphthyl optionally substituted with halogen atoms, alkoxy having 1 to 3 carbon atoms, or trifluoromethyl, or phenylalkyl having 7 to 9 carbon atoms, optionally substituted on the aromatic ring with halogen, alkoxy having 1 to 3 carbon atoms, or trifluoromethyl, or
$R_7$ and $R_8$, together with the nitrogen atom to which they are linked, form a five- or six-membered heterocyclic radical selected from piperazinyl, morpholinyl, piperidinyl, and pyrrolidinyl, and optionally substituted with alkyl having 1 to 5 carbon atoms, with alkoxy carbonyl having 2 to 6 carbon atoms, or with phenyl, phenylalkyl having 7 to 9 carbon atoms, pyridyl or benzhydryl, these radicals optionally being substituted on the aromatic ring or rings with a substituent selected from halogen, hydroxyl, alkyl, or alkoxy having 1 to 4 carbon atoms, nitro, and trifluoromethyl,
alkyl containing 1 to 5 carbon atoms, optionally substituted with radical selected from the group consisting of hydroxyl, oxo, and cyano, and alkoxycarbonyl containing 2 to 4 carbon atoms;
$R_2$ represents:
 hydrogen
 alkyl having 1 to 5 carbon atoms
 phenyl sulfonyl in which phenyl is optionally substituted with alkyl having 1 to 5 carbon atoms in a straight or branched chain,
 an alkyl carbonyl radical having 2 to 3 carbon atoms, a radical of the formula:

in which
R$_9$ represents alkyl having 1 to 6 carbon atoms, phenyl, naphthyl or phenylalkyl having 7 to 9 carbon atoms, these groups being optionally substituted on the aromatic ring with halogen, alkoxy having 1 to 3 carbon atoms, or trifluoromethyl);

and R$_3$ and R$_4$ represent:
each simultaneously a hydrogen atom or together an oxygen atom, and a salt thereof with a pharmaceutically acceptable acid.

2. An isomer, diastereoisomer or enantiomer of a compound of claim 1, isolated or in the form of a mixture.

3. A compound as claimed in claim 1 which is 6-hydroxy-5,6-dihydro-4-oxo-4H-pyrrolo[1,2-a]thieno-[2,3-f][1,4]diazepine.

4. A compound as claimed in claim 1 which is 6-methoxy-5,6-dihydro-4-oxo-4H-pyrrolo[1,2-a]thieno-[2,3-f][1,4]diazepine.

5. A compound as claimed in claim 1, which is 6-methoxycarbonylmethylmercapto-5,6-dihydro-4-oxo-4H -pyrrolo[1,2-a]thieno[2,3-f][1,4]diazepine.

6. A compound as claimed in claim 1, which is selected from 6-methylamino-5,6-dihydro-4-oxo-4H-pyrrolo[1,2-a]thieno -[2,3-f][1,4]diazepine, and its addition salts with a pharmaceutically-acceptable inorganic or organic acid.

7. A compound as claimed in claim 1, which is 5,6-dihydro-4-oxo-4H-pyrrolo[1,2-a]thieno[2,3-f][1,4]diazepine.

8. A compound as claimed in claim 1, which is 6-acetonyl-5,6-dihydro-4-oxo-4H-pyrrolo[1,2-a]thieno-[2,3-f][1,4]diazepine.

9. A compound as claimed in claim 1, which is 6-(2-hydroxypropyl)-5,6-dihydro-4-oxo-4H-pyrrolo[1,2-a]thieno -[2,3-f][1,4]diazepine.

10. A compound as claimed in claim 1, which is 6-[ethoxycarbonyl(cyano)methyl]-5,6-dihydro-4-oxo-4H -pyrrolo[1,2-a]thieno[2,3-f][1,4]diazepine.

11. A compound as claimed in claim 1, which is 6-[methoxycarbonyl(cyano)methyl]-5,6-dihydro-4-oxo-4H -pyrrolo[1,2-a]thieno[2,3-f][1,4]diazepine.

12. A compound as claimed in claim 1, which is 6-[1-(ethoxycarbonyl)acetonyl]-5,6-dihydro-4-oxo-4H-pyrrolo -1,2-a]thieno[2,3-f][1,4]diazepine.

13. A compound as claimed in claim 1, which is selected from 5,6-dihydro-4H-pyrrolo[1,2-a]thieno[2,3-f][1,4]diazepine, and its addition salts with a pharmaceutically-acceptable inorganic or organic acid.

14. A compound as claimed in claim 1, which is 5-(p.tolylsulfonyl)-5,6-dihydro-4H-pyrrolo[1,2-a]thieno -[2,3-f][1,4]diazepine.

15. A compound as claimed in claim 1, which is 5-acetyl-5,6-dihydro-4-oxo-4H-pyrrolo[1,2-a]thieno [2,3-f][1,4]diazepine.

16. A compound as claimed in claim 1, which is 5-(N-phenylcarbamoyl)-5,6-dihydro-4-oxo-4H-pyrrolo -[1,2-a]thieno [2,3-f][1,4]diazepine.

17. A compound as claimed in claim 1, which is 6-phenacyl-5,6-dihydro-4-oxo-4H-pyrrolo[1,2-a]thieno [2,3-f][1,4]diazepine.

18. A compound as claimed in claim 1, which is selected from 6-morpholino-5,6-dihydro-4-oxo-4H-pyrrolo[1,2-a]thieno -[2,3-f][1,4]diazepine, and its addition salts with a pharmaceutically-acceptable inorganic or organic acid.

19. A compound as claimed in claim 1, which is selected from 6-pyrrolidino-5,6-dihydro-4-oxo-4H-pyrrolo[1,2-a]thieno -[2,3-f][1,4]diazepine, and its addition salts with a pharmaceutically-acceptable inorganic or organic acid.

20. A pharmaceutical composition useful in treatment of metabolic ailments containing as active principle an effective amount of a compound as claimed in any one of claims 1 to 21, in combination with a pharmaceutically-acceptable, excipient or vehicle.

21. A method for treating a living animal afflicted with an ailment selected from cerebral aging, stroke, ischemic syndromes or metabolic diseases including hyperlipidemia, hypertriglyceridemia, hyperglycemia and hypercholesterolemia comprising the step of administering to the said living animal an amount of a compound of claim 1 which is effective for alleviation of the said condition.

* * * * *

UNITED STATES PATENT AND TRADEMARK OFFICE
CERTIFICATE OF CORRECTION

PATENT NO. : 5,130,301

DATED : Jul. 14, 1992

INVENTOR(S) : Sylvain Rault, Michle Boulouard, Max Robba,
Béatrice Guardiola, Michelle Devissaguet It is certified that error appears in the above-identified patent and that said Letters Patent is hereby corrected as shown below:

Title Page, [56], References Cited, PUBLICATIONS, 2nd and 3rd line; move the closing parenthesis from line 3 to the end of line 2.

Title Page, [56], References Cited, PUBLICATIONS, line 3; "-4-" should read -- -1,4- --.

Column 7, approximately line 41; "LialH," should read --$LiAlH_4$,--.

Column 7, approximately line 66/67; move the closing parenthesis ")" to the previous line and insert before the hyphen "-".

Column 13, approximately line 46; "3160" should read -- 3010 --.

Column 17, approximately line 43/44; "4---oxo" should read -- 4-oxo --.

Column 19, approximately line 25; "a yield." should read -- a 16% yield. --.

Column 29, above TABLE VI AND TABLE VII, insert the heading; --NMR parameters relating to the compounds of Examples 25 to 27 corresponding to the formulae Ij to Il. --.

Column 31, line 62; "or option-"should read -- or furyl option---.

Column 31, line 65; "atoms option-" should read --atoms, option- --.

Column 31, line 68; insert a comma after "trifluoromethyl".

Column 32, line 35; "represent a hydrogen," should read -- represent hydrogen --.

Column 32, line 38; "halogen atoms, alkoxy" should read -- halogen, alkoxy --.

Column 32, line 52; "atoms, pyridyl or benzhydryl," should read -- atoms, or benzhydryl, --.

Column 32, line 58; "with radical" should read -- with a radical--.

Column 32, line 59; "oxo, and cyano," should read --oxo, cyano, --.

UNITED STATES PATENT AND TRADEMARK OFFICE
CERTIFICATE OF CORRECTION

PATENT NO. : 5,130,301

DATED : Jul. 14, 1992

INVENTOR(S) : Sylvain Rault, Michel Boulouard, Max Robba
Béatrice Guardiola, Michelle Devissaguet It is certified that error appears in the above-identified patent and that said Letters Patent is hereby corrected as shown below:

Column 32, line 66; delete "in a straight or branched chain".

Column 32, line 67; delete "an" and "radical".

Column 33, line 9; "naphthyl or" should read --naphthyl, or--.

Column 33, line 17; "pharmaceutically acceptable" should read -- pharmaceutically-acceptable --.

Signed and Sealed this

Nineteenth Day of October, 1993

Attest:

BRUCE LEHMAN

Attesting Officer      Commissioner of Patents and Trademarks